(12) United States Patent
Miyazawa et al.

(10) Patent No.: US 7,503,245 B2
(45) Date of Patent: Mar. 17, 2009

(54) METHOD AND DEVICE FOR MANUFACTURING TISSUE SECTION

(75) Inventors: Kazuo Miyazawa, Koushoku (JP); Iwao Kuroiwa, Koushoku (JP); Masahiko Arakawa, Koushoku (JP); Akira Yanagimachi, Koushoku (JP)

(73) Assignee: Sakura Seiki Co., Ltd., Chikuma-shi (JP)

( * ) Notice: Subject to any disclaimer, the term of this patent is extended or adjusted under 35 U.S.C. 154(b) by 488 days.

(21) Appl. No.: 10/509,743

(22) PCT Filed: Mar. 26, 2003

(86) PCT No.: PCT/JP03/03758

§ 371 (c)(1),
(2), (4) Date: Sep. 30, 2004

(87) PCT Pub. No.: WO03/083445

PCT Pub. Date: Oct. 9, 2003

(65) Prior Publication Data

US 2005/0126311 A1    Jun. 16, 2005

(30) Foreign Application Priority Data

Apr. 1, 2002    (JP) .............................. 2002-098830

(51) Int. Cl.
*B26D 1/00* (2006.01)

(52) U.S. Cl. .............................. 83/13; 83/915.5; 83/155

(58) Field of Classification Search .................... 83/13, 83/919.5, 28, 78, 155, 162, 707, 915.5
See application file for complete search history.

(56) References Cited

U.S. PATENT DOCUMENTS 3,552,247 A * 1/1971 Pickett .......................... 83/24
3,690,988 A * 9/1972 Ullberg ....................... 156/353

(Continued)

FOREIGN PATENT DOCUMENTS

EP          0 088 549 A1      9/1983

(Continued)

*Primary Examiner*—Kenneth E. Peterson
*Assistant Examiner*—Phong Nguyen
(74) *Attorney, Agent, or Firm*—Birch, Stewart, Kolasch & Birch, LLP (57) ABSTRACT

The method for manufacturing a tissue section, which is used for a sample for observation by a microscope, comprises the steps of slicing an organism specimen (12), whose form has been fixed by freezing or by using an embedding agent, along a slicing surface, characterized by: adjusting a distance between the slicing surface of the organism specimen (12) and one side of a tape (32) and a temperature difference between the organism specimen (12) and the tape (32) when the slicing of the organism specimen (12) is started, thereby a tip part of the tissue section (16) curling to the outside of the slicing surface of the organism specimen (12) is allowed to adhesively abut on one side of the tape (32) running apart from the slicing surface of the organism specimen (12); and running the tape (32) at a speed in synchronism with a slicing speed of the tissue section (16) after the tip part of the tissue section (16) is allowed to adhesively abut on the one side of the tape (32), thereby the entire tissue section (16) cut off from the organism specimen (12) can be adhered onto the one side of the tape (32).

18 Claims, 5 Drawing Sheets

U.S. PATENT DOCUMENTS

| | | | |
|---|---|---|---|
| 3,733,948 A | * 5/1973 | Pickett | 83/98 |
| 5,156,019 A | * 10/1992 | McCormick | 62/320 |
| 5,960,640 A | 10/1999 | Teppke | |

FOREIGN PATENT DOCUMENTS

| | | |
|---|---|---|
| JP | 04-177143 A | 6/1992 |
| JP | 07-159298 A | 6/1995 |
| JP | 09-101242 A | 4/1997 |
| JP | 09-304246 A | 11/1997 |
| JP | 2000-346764 A | 12/2000 |
| JP | 2002-022626 A | 1/2002 |
| JP | 2002-031586 A | 1/2002 |
| JP | 2003-004604 A | 1/2003 |

* cited by examiner

METHOD AND DEVICE FOR MANUFACTURING TISSUE SECTION

FIELD OF TECHNOLOGY

The present invention relates to a method and a device for manufacturing a tissue section, more precisely relates to a method and a device for manufacturing a tissue section, which is used for a sample for observation by a microscope and made by slicing an organism specimen, whose form has been fixed by freezing or by using an embedding agent, along a slicing surface.

BACKGROUND TECHNOLOGY

Pathological samples are observed by the steps of: slicing an organism specimen to form tissue sections, adhering the tissue sections onto slide glasses to form the pathological samples; and observing the samples by a microscope.

To observe by the microscope, the tissue sections must be thin so as to allow lights to pass through them. Thus, a form of the organism specimen, from which the tissue sections are cut, has been previously fixed by freezing or by using an embedding agent, e.g., paraffin, so as to easily slice the organism specimen.

Figure 5:
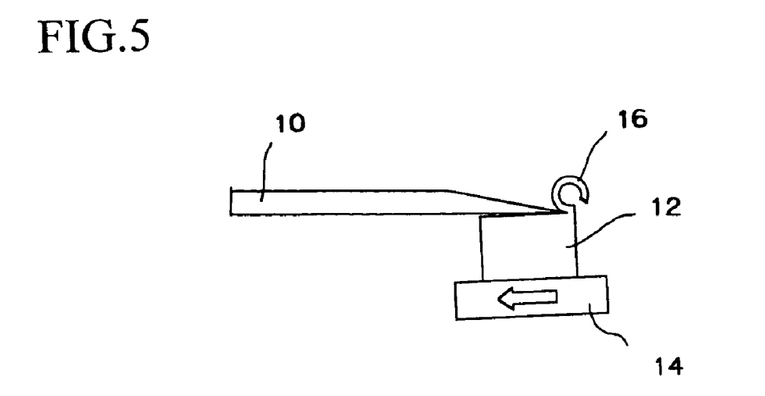
FIG. 5 is an explanation view explaining the tissue section 16, which has been cut off from the frozen organism specimen 12 and which curls to outside of the slicing surface of the frozen organism specimen 12.

However, even if the form of the organism specimen is fixed by freezing or by using the embedding agent as shown in FIG. 5, the tissue section 16 (upwardly) curls to the outside of a slicing surface of the organism specimen 12 when the organism specimen 12, which is mounted on a table 12 and whose form is fixed, is moved in a direction of an arrow and cut by a fixed knife 10.

When the curling tissue section 16 is mounted on a flat slide glass, creases are formed, a bad sample for microscope observation is often produced.

Especially, degree of curling of the tissue section 16, which is made by slicing the organism specimen 12 whose form has been fixed by freezing (hereinafter sometimes referred to "frozen organism specimen 12") is sometimes greater than that of the tissue section 16, which is made by slicing the organism specimen 12 whose form has been fixed by the embedding agent, e.g., paraffin, (hereinafter sometimes referred to "embedded organism specimen 12").

The tissue sections 16 for an urgent pathological examination is usually cut from the frozen organism specimen 12 because there is no time to fix the form by the embedding agent, e.g., paraffin.

Figures 6A, 6B:
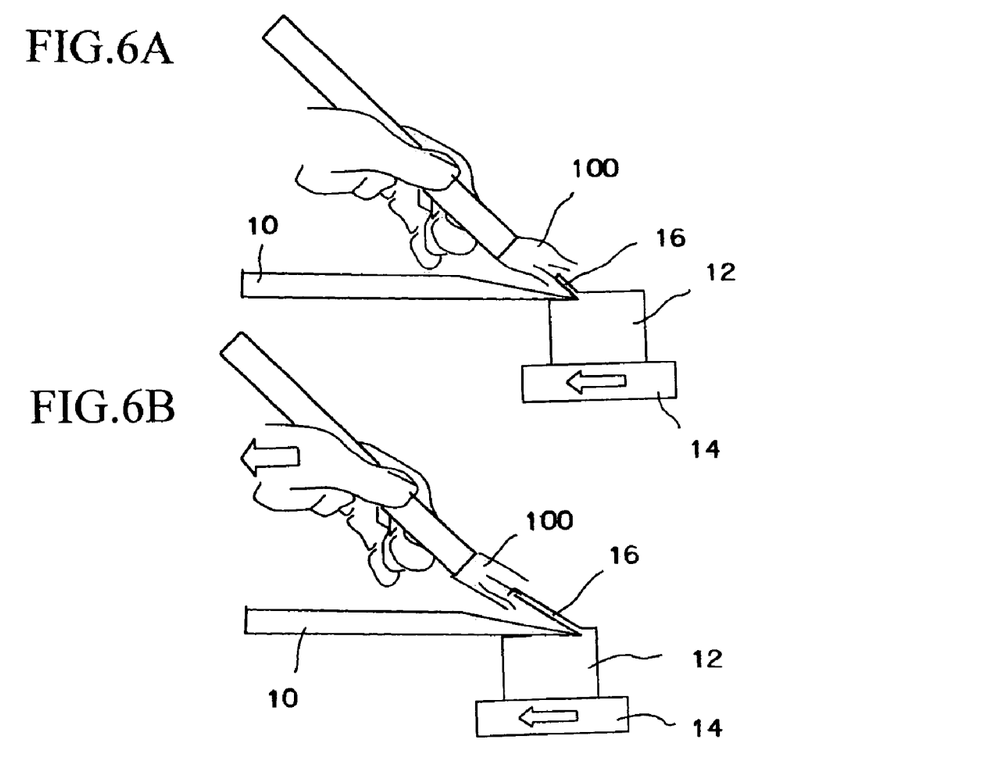
FIGS. 6A and 6B are explanation views explaining the conventional method of collecting the tissue section 16, in which the curl is manually restricted.

Conventionally, as shown in FIG. 6A, the table 14, on which the frozen organism specimen 12 is mounted, is moved in the direction of the arrow, and the tissue section 16, which has been cut by the fixed knife 10, is manually adhered to a tip part of a brush 100, then the brush 100 holding the tissue section 16 at the tip part is synchronously moved with a slicing speed, as shown in FIG. 6B, so as to restrict the curl of the tissue section 16.

To manually perform the steps shown in FIGS. 6A and 6B, enough skill is required, and it is often impossible to reobtain the same frozen organism specimen 12, from which the tissue section 16 will be cut. Therefore, miscutting the tissue section 16 is not allowed, so a worker must cut carefully. Further, there is a risk of infection from the frozen organism specimen 12.

To execute a rapid and correct diagnosis on the basis of a rapid examination of the tissue section 16 cut from the frozen organism specimen 12, experienced pathological doctors are required, so hospitals, which are capable of rapidly examining the frozen organism specimens 12, are limited.

In the case of treating the embedded organism specimen 12 too, it is difficult for a nonskilled worker to manually perform the steps shown in FIGS. 6A and 6B, it is often impossible to reobtain the same embedded organism specimen 12, from which the tissue section 16 will be cut, and miscutting the tissue section 16 is not allowed, so a worker must cut carefully as well as the frozen organism specimen 12.

To solve the disadvantages, some methods for manufacturing tissue sections from the conventional organism specimens 12 are disclosed in, for example, Japanese Patent Gazettes NO. 4-177143, No. 7-159298 and No. 2002-31586, in each of which an adhesive face of a transparent film is adhered on the organism specimen, the organism specimen is sliced immediately under the transparent film by, for example, a knife, then the tissue section is taken out together with the transparent film. In the patent gazettes No. 4-177143 and No. 7-159298, the transparent film is pressed onto the organism specimen by a roller or a plunger when the transparent film is adhered onto the organism specimen.

Further, in a Japanese Patent Gazette No. 6-323967, a tissue section, which has been cut from an organism specimen, is dipped into water, then the tissue section floating on a water surface is scooped up by a transparent film.

By employing the methods disclosed in the patent gazettes, the tissue section can be adhered onto one side of the transparent film without manually performing the difficult steps shown in FIGS. 6A and 6B.

However, since the adhesive face of the transparent film is pressed onto the organism specimen, an adhesive directly contacts the organism specimen so that tissue cells, which are in and near the contact surface of the organism specimen, are sometimes badly influenced and transformed.

Further, if air is left in a space between the transparent film and the organism specimen, creases are easily formed in the tissue section cut off from the organism specimen, so that it is necessary to discharge the air by pressing the transparent film onto the organism specimen with a prescribed force. Tissue cells of the organism specimen are easily broken by pressing the transparent film, and thickness of the tissue section, which is cut off from the organism specimen, is partially varied by repeatedly pressing and releasing the organism specimen.

When a plurality of tissue sections are sliced off from one organism specimen to manufacture a plurality of microscopic samples, transparent films are pressed onto the organism specimen for each slice so as to discharge air. Further, the tissue sections must be adhered on one side of the transparent film in slicing order so as to individually recognize the tissue sections.

Therefore, the steps until adhering the tissue sections on the one side of the transparent film in the slicing order are included in a rate-controlling stage of manufacturing microscopic samples.

In the method such that the tissue section is scooped from water by the transparent film, frozen organism specimens cannot be used, so the method is limited to organism specimens embedded by a hydrophobic embedding agent, e.g., paraffin.

Further, in the case of using the embedded organism specimens embedded by the hydrophobic embedding agent, e.g., paraffin, if a plurality of tissue sections are dipped into water, it is difficult to individually recognize them, so one tissue section is dipped into the water after the prior tissue section is scooped by the transparent film. Therefore, the step of making the tissue sections is the rate-controlling stage of manufacturing microscopic samples.

An object of the present invention is to provide a method and a device for manufacturing a tissue section, which are capable of treating a frozen organism specimen and an embedded organism specimen and rapidly adhering the tissue section onto a film without pressing the film.

DISCLOSURE OF THE INVENTION

The inventors of the present invention have studied and found that a tip part of a tissue section curls to outside of a slicing surface of an organism specimen when slicing the organism specimen is started. Further, they found that the tissue section can be rapidly adhered onto a film without pressing the tissue section onto the film by adhesively abutting the tip part of the tissue section on one side of the film running apart from the organism specimen and running the film at a speed in synchronism with a slicing speed of the tissue section, so that they have invented the present invention.

Namely, the method for manufacturing a tissue section, which is used for a sample for observation by a microscope, comprises the steps of slicing an organism specimen, whose form has been fixed by freezing or by using an embedding agent, along a slicing surface, is characterized by: adjusting a distance between the slicing surface of the organism specimen and one side of a film and a temperature difference between the organism specimen and the film when the slicing of the organism specimen is started, thereby a tip part of the tissue section curling to the outside of the slicing surface of the organism specimen is allowed to adhesively abut on one side of the film running apart from the slicing surface of the organism specimen; and running the film at a speed in synchronism with a slicing speed of the tissue section after the tip part of the tissue section is allowed to adhesively abut on the one side of the film, thereby the entire tissue section cut off from the organism specimen can be adhered onto the one side of the film.

And, the device for manufacturing a tissue section, which is used for a sample for observation by a microscope, comprising: means for slicing an organism specimen, whose form has been fixed by freezing or by using an embedding agent, along a slicing surface; and means for running a film apart from the slicing surface of the organism specimen, is characterized by: means for adjusting a distance between the slicing surface of the organism specimen and one side of the film so as to make a tip part of the curling tissue section contact with the outside of the slicing surface of the organism specimen when the slicing of the organism specimen is started; means for adjusting temperature between the organism specimen and the film so as to make the tip part of the tissue section, which has been contacted the outside of the film, adhesively abut on the film; and means for synchronizing a slicing speed of the tissue section, whose tip part has been adhered on the one side of the film, and a running speed of the film so as to adhere the entire tissue section cut off from the organism specimen onto the one side of the film.

In the present invention, the temperature difference between the organism specimen and the film may be adjusted by adjusting temperature of the film and/or temperature of an atmosphere, in which the organism specimen is sliced, so that the temperature difference between the organism specimen and the film can be easily adjusted. Preferably, temperature of the film is adjusted to temperature, at which a part of an ice or the embedding agent for fixing the form of the organism specimen melts and the tissue section is adhered onto the film.

Temperature of an atmosphere, in which the organism specimen is sliced, may be adjusted so as to hold the fixed form of the organism specimen, so that slicing the organism specimen can be performed stably.

A plurality of rollers including a close roller, which is provided nearest to the slicing surface of the organism specimen, may be provided in a film running path, and the distance between the slicing surface of the organism specimen and the one side of the film may be adjusted by moving the close roller to and away from the slicing surface of the organism specimen, so that the distance between the slicing surface of the organism specimen and the one side of the film can be easily adjusted.

If a center of the close roller is moved on a bisector line of an intersection angle between a line extended from a cutting surface of a cutting tool, which intersects a line extended from the slicing surface of the organism specimen, and the line extended from the slicing surface of the organism specimen, the close roller never interferers with cutting means and the slicing surface of the organism specimen.

Further, the film running speed with respect to the slicing speed of the tissue section is adjusted so as not to form creases in the tissue section and break the tissue section, namely, preferable ratio (Vt/Vs) of the film running speed (Vt) to the slicing speed (Vs) of the tissue section is 1.2-0.8.

Note that, if the film is a transparent film, the tissue section adhered on the transparent film can be used as a microscopic sample.

In the present invention, since the tip part of the tissue section curls to outside of the slicing surface of the organism specimen when the slicing of the organism specimen is started, so that the entire tissue section cut off from the organism specimen can be adhered onto the one side of the film running apart from the slicing surface of the organism specimen.

Namely, when the slicing of the organism specimen is started, the tip part of the tissue section curling to the outside of the slicing surface of the organism specimen abuts on the one side of the film running apart from the organism specimen. The temperature difference between the organism specimen and the film has been adjusted so as to adhere the tip part of the tissue section on the one side of the film.

Therefore, the tissue section, whose tip part has been adhered on the one side of the film, can be entirely adhered onto the one side of the film by running the film at the speed in synchronism with the slicing speed of the tissue section.

As described above, since the entire tissue section can be rapidly adhered on the film running apart from the organism specimen, the film is not pressed onto the organism specimen, so that no tissue cells of the organism specimen are broken and the tissue section having uniform thickness can be stably manufactured.

Further, since the adhesion of the tissue section is controlled on the basis of the temperature difference between the film and the organism specimen, no adhesive is applied to the one side of the film so that no tissue cells are badly influenced and transformed by adhesive.

In the present invention, the tissue section is immediately adhered onto the film after the tissue section is cut off from the organism specimen; even if a plurality of the tissue sections are sliced, the tissue sections can be adhered onto the film in slicing order, so that the tissue section can be easily individually recognized.

PREFERRED EMBODIMENTS OF THE INVENTION

Figure 1:
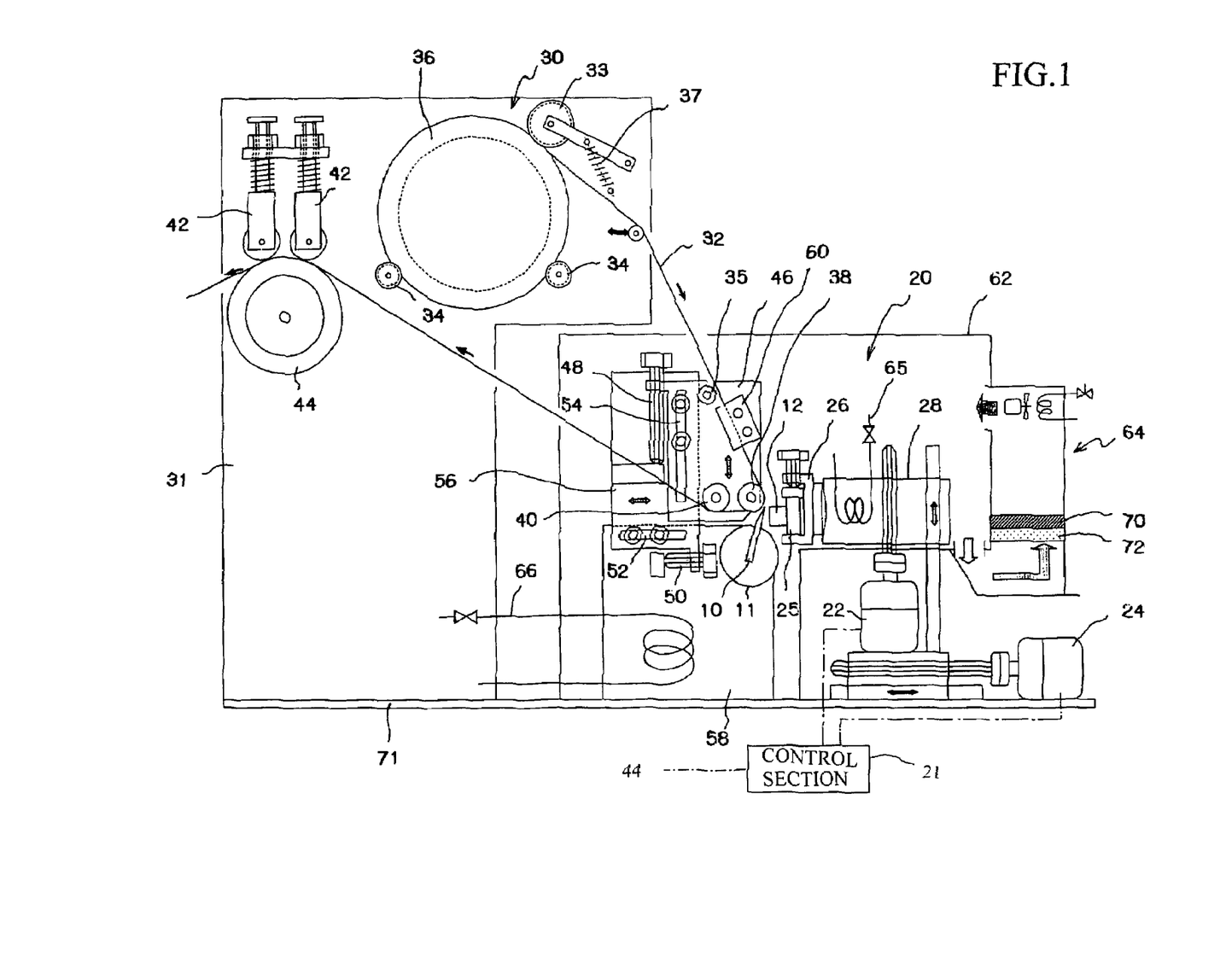
FIG. 1 is a schematic view of a tissue section manufacturing device of an embodiment of the present invention.

A tissue section manufacturing device of an embodiment of the present invention is shown in FIG. 1. FIG. 1 is a schematic view of the device, which manufactures the tissue section from a frozen organism specimen.

The device shown in FIG. 1 has slicing means 20, which slices a frozen organism specimen 12 along a slicing surface. The slicing means 20 comprises: a holding section 28 including a clamper 26 for holding a jig 25, to which the frozen organism specimen 12 is fixed; a servo motor 22 for vertically moving the holding section 28 as driving means; and a servo motor 24 for moving the holding section 28 rightward and leftward. Further, a knife 10 for slicing the frozen organism specimen 12 is provided to a rotatable cylinder 11, and an angle of the knife 10 with respect to the slicing surface of the frozen organism specimen 12 can be adjusted by the cylinder 11.

Running means 30 makes a tape 32, which is made of a transparent film (hereinafter sometimes referred to "the tape 32"), run apart from the slicing surface of the frozen organism specimen 12. The running means 30 is provided to an attachment board 31, which is vertically provided on a base 71, and an attachment plate 46, which is separated from the attachment board 31.

Guide rollers 34 and 34, which support a tape cylinder 36 on which the tape 32 is wound, pressing rollers 42 and 42, which hold the tape 32 with a driving roller 44, and a braking roller 33, which is biased by a spring 37 so as to contact the tape cylinder 36 with a prescribed force, are provided to the attachment board 31. Prescribed tension is given to the tape 32 between the braking roller 33 and the driving roller 44.

Further, a guide roller 35, which guides the tape 32 extended from the tape cylinder 36, a close roller 38, which is located nearest to the slicing surface of the frozen organism specimen 12, and a guide roller 40 are provided to the attachment plate 46.

The guide roller 40 adjusts an angle of the tape 32 with respect to the close roller 38, and a position of the guide roller 40 is adjusted so as to easily adhere tissue sections, which are sliced off from the frozen organism specimen 12 by the knife 10, to the tape 12.

By employing the running means 30, the tape 32, which has been drawn from the tape cylinder 36 with prescribed tension by the driving roller 44, is wound by a collecting roller (not shown) via the guide roller 35, the close roller 38, which is located nearest to the slicing surface of the frozen organism specimen 12, the guide roller 40 and a space between the pressing rollers 42, 42 and the driving roller 44.

Note that, a preferable diameter of the close roller 38 is 2-40 mm.

The device shown in FIG. 1 has means for adjusting a distance between the tape 32, which is driven by the running means 30, and the frozen organism specimen 12. The distance adjusting means is constituted by: a plate 56, which is attached to a base member 58 by screws; and an attachment plate 46, which is attached to the plate 56 by screws inserted in a vertical slit 54.

Further, the device has a screw 48, which moves the plate upward and downward when the screws inserted in the vertical slit 54 are loosened, and a screw 50, which moves the plates 56 and 46, which are integrated by driving the screws in the slit 54 of the plate 46, rightward and leftward.

When the knife 10 starts to slice the frozen organism specimen 12 the distance by the distance adjusting means adjusts the slicing surface of the frozen organism specimen 12 and the tape 32 so as to make a tip part of the tissue section 16, which has curled to outside of the slicing surface of the frozen organism specimen 12, contact the tape.

In the device shown in FIG. 1, the close roller 38, which is located nearest to the slicing surface of the frozen organism specimen 12, is moved so as to adjust the distance between the tape 32, which is guided by the close roller 38, and the slicing surface of the frozen organism specimen 12.

Figure 2:
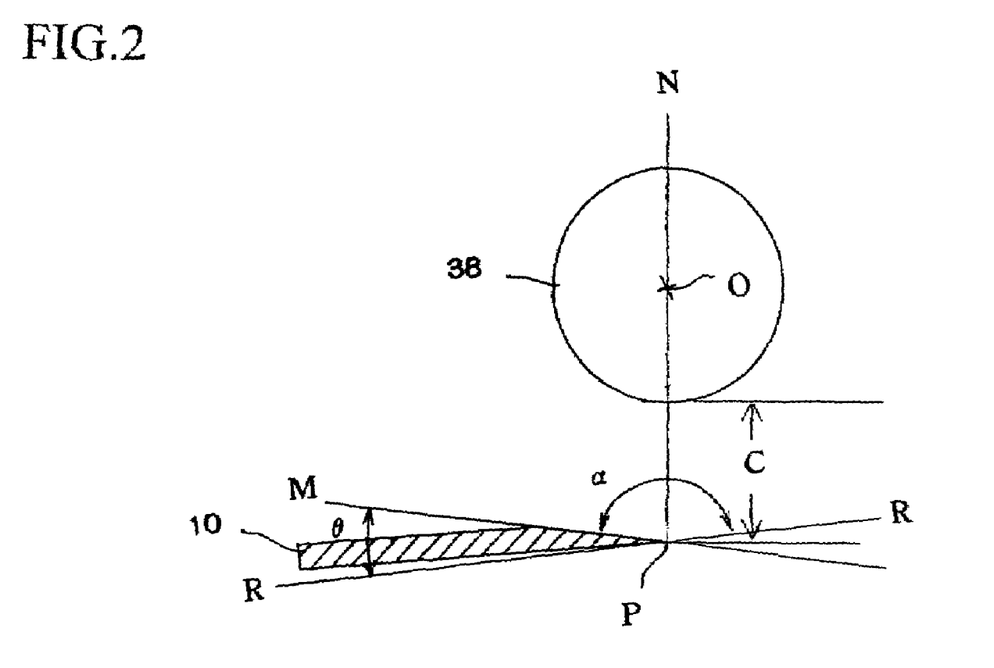
FIG. 2 is an explanation view explaining a method of adjusting a distance C between a close roller 38 of the device shown in FIG. 1 and a slicing surface of an organism specimen 12.

As shown in FIG. 2, a shortest distance C between a slice starting point P, at which an edge of the knife 10 contacts the slicing surface of the frozen organism specimen 12 and starts the slice, and the close roller 38 by moving the close roller 38.

When the distance C is adjusted, preferably the center O of the close roller 38 is moved on a bisector line N of an intersection angle α between a line M extended from a cutting surface of the knife 10, which intersects a line R extended from the slicing surface of the organism specimen 12 at an angle θ, and the line R extended from the slicing surface of the organism specimen, which intersect at the slice starting point P, so as to prevent the close roller 38 from interfering with the knife 10 and the slicing surface of the frozen organism specimen 12.

Note that, the guide roller 40, which is attached to the plate 46 to which the close roller 38 is attached, is moved together with the close roller 38 when the distance between the tape 32, which is guided by the close roller 38, and the slicing surface of the frozen organism specimen 12.

Further, the device shown in FIG. 1 has means for adjusting temperature difference between the tape 32 and the organism specimen 12 so as to allow the tip part of the tissue section 16 to adhesively abut on one side of the tape 32.

The temperature adjusting means comprises: a heater 60, which is provided in a tape running path and which heats the tape 32 to prescribed temperature; a temperature control unit 64, which circulates air in an insulating box 62, which insulates the slicing means 20, the knife 10, the close roller 38, etc., and maintains temperature of the air at the prescribed temperature; and heat exchanging tubes 65 and 66, which cools the slicing means 20 and the knife 10 so as to maintain a form of the frozen organism specimen 12. The heat exchanging tube 65 cools the holding section 28, which includes the clamper 26 for holding the jig 25 to which the frozen organism specimen 12 is fixed; the heat exchanging tube 66 cools the knife 10 and a part of the cylinder 11. Further, The temperature control unit 64 has a disinfecting filter 70 and a prefilter 72 so as to cool and disinfect the air circulating in the insulating box 62.

In the temperature adjusting means, the tissue section 16 (see FIG. 5) can be sliced off from the frozen organism specimen 12 in an atmosphere, in which temperature is maintained to maintain the form of the frozen organism specimen 12, by the temperature control unit 64 and the heat exchanging tubes 65 and 66. To manufacture the good tissue section 16 by slicing the frozen organism specimen 12, preferable temperature of the knife 10 and the frozen organism specimen 12 are −1° C.--−40° C.

On the other hand, when the tape 32 is guided by the close roller 38, the tape is heated by a heater 60 provided in the insulating box 62 so as to adhere the tissue section 16, which contacts the tape. The heater 60 may be a known heater, e.g., heat block, cartridge heater, tape heater.

To adhere the entire tissue section 16 onto the tape 32, whose temperature has been adjusted, without breaking and forming creases, it is necessary to run the tape 32, on which the tip part of the tissue section 16 has been adhesively abut, at a speed in synchronism with a slicing speed of the tissue section 16.

Thus, in the device shown in FIG. 1, a control section 21 acts as means for synchronizing the running speed of the tape 32 with the slicing speed of the tissue section 16 is constituted by a servo motor (not shown) for driving the driving roller 44 and a servo motor 22 for vertically moving the holding section 28 and cutting the tissue section 16 off from the frozen organism specimen 12 with the knife 10.

In this description, the word "synchronization" means to move the tape 32, to which the tip part of the tissue section 16 has been adhesively abut, with respect to the slicing speed of the tissue section 16, at the running speed such that no breaks and no creases are formed in the tissue section. Preferably, the servo motor 22 is controlled to make ratio (Vt/Vs) of the running speed (Vt) of the tape 32 to a running speed (Vs) of the holding section 28 1.2-0.8.

Note that, the servo motors assembled in the device shown in FIG. 1 may be replaced with linear motors, stepping motors, etc.

In the device shown in FIG. 1, when the tissue section 16 is sliced off from the frozen organism specimen 12, firstly the frozen organism specimen 12 is made by directly freezing the specimen in liquid nitrogen or dry ice-acetone or by freezing the specimen, which has been embedded by an adhesive liquid including an ice crystal-inhibitor and carboxymethylcellulose (CMC), therein. To fix the frozen organism specimen 12 to the jig 25, the frozen organism specimen 12 is fixed by an ice crystal-inhibitor.

Carboxymethylcellulose may be mixed with the ice crystal-inhibitor, or an OCT compound, which is commercially sold, may be used.

The jig 25, to which the frozen organism specimen 12 has been fixed, is fixed to the clamper 26 of the holding section 28, then the cylinder 11 is turned to adjust the angle θ (see FIG. 2) between the cutting surface of the knife 10 and the slicing surface of the frozen organism specimen 12.

Next, the close roller 38 is moved by the screws 48 and 50 to adjust the distance C shown in FIG. 2, which is the shortest distance between the close roller 38 and the frozen organism specimen 12, so that the tip part of the tissue section 16, which has curled to outside of the slicing surface, can adhesively abut, when the knife 10 starts to slice the frozen organism specimen 12.

As shown in FIG. 2, when the close roller 38 is moved, the center O of the close roller 38 is moved on a bisector line N of the intersection angle α between the line M extended from the cutting surface of the knife 10, which intersects the line R extended from the slicing surface of the organism specimen 12 at the angle θ, and the line R extended from the slicing surface of the organism specimen, which intersect at the slice starting point P, so that interference among the close roller, the knife 10 and the slicing surface of the frozen organism specimen 12 can be avoided.

The tape 32, which has been drawn from the tape cylinder 36, is manually engaged with the guide roller 35, the heater 60, the close roller 38, the guide roller 40, the driving roller 44 and the collecting roller (not shown).

Next, the device shown in FIG. 1 is turned on, then the driving roller 44 is driven to run the tape 32, the heater 60, which is located between the tape cylinder 36 and the close roller 38 and in the insulating box 42, heats the running tape 32 and adjusts the temperature of the tape 32 guided by the close roller 38 to prescribed temperature, at which a part of ice fixing the form of the frozen organism specimen 12 is melted to allow the tissue section 16 to adhesively abut on the tape 32, e.g., 0-40° C. (preferably 10-30° C.).

Simultaneously, the temperature control unit 64 cools the entire insulating box 62, the heat exchanging tube 65 for cooling the frozen organism specimen 12 and the heat exchanging tube 66 for cooling the knife 10 so as to maintain temperature of an atmosphere of slicing the frozen organism specimen 12 in a range of −1--−40° C.

Further, the servo motor 24 is started to move the holding section 28, which has the clamper 26 for holding the jig 25 to which the frozen organism specimen 12 has been fixed, rightward or leftward a prescribed distance, so that thickness of the tissue section 16 sliced off from the frozen organism specimen 12 is defined. The moving distance of the holding section 28, which is moved rightward and leftward by the servo motor 24, has been previously inputted to the control section 21, which controls the servo motor 24.

Then, the servo motor 22 is started to move the holding section 28 upward or downward so as to slice the tissue section 16 off from the frozen organism specimen 12 by the knife 10. The control section 21 synchronizes the servo motor 22 with the servo motor (not shown) for driving the driving roller 44 so as to synchronize the slicing speed of the tissue section 16 with the running speed of the tape 32, so that no crease are formed in the tissue section 16.

A manner for adhering the tissue section 16, which has been sliced off from the frozen organism specimen 12 by the knife 10 with the prescribed thickness, onto the running tape 32 will be explained with reference to FIGS. 3A-3E.

In FIG. 1, the jig 25, to which the frozen organism specimen 12 is fixed, is moved upward and downward, but it is moved rightward and leftward in FIGS. 3A-3E.

Figure 3A:
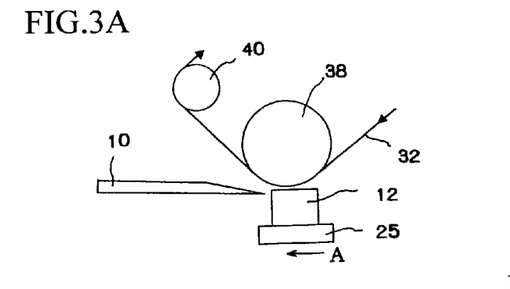
FIGS. 3A-3E are explanation views, in which a tissue section 16, which has been sliced by a knife 10, is adhered onto a tape 32 made of a transparent film.

Firstly, the jig 25 is moved in a direction of an arrow A so as to move the frozen organism specimen 12 toward a front tip the fixed knife 10 [FIG. 3A]. At that time, the tape 32 is already started to run in the moving direction of the jig 25.

Figure 3B:
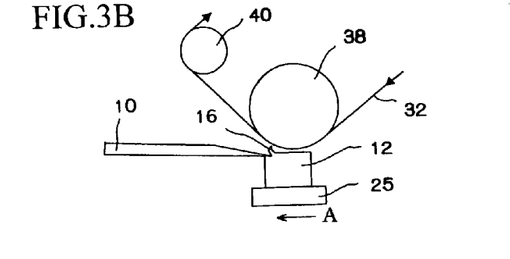

The jig 25 is further moved in the direction of the arrow A, then the front tip of the knife 10 bites the frozen organism specimen 12 so as to start to slice the tissue section 16 [FIG. 3B].

Figure 3C:
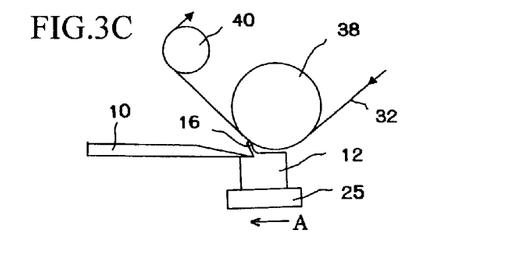

The sliced tissue section 16 is guided by a sloped cutting surface of the knife 10, and it curls to outside of the slicing surface of the frozen organism specimen 12, then the tip part thereof contacts the tape 32, which is guided by the close roller 38 [FIG. 3C]. Temperature of the tape 32 engaging with the close roller 38 is adjusted, by the heater 60 shown in FIG. 1, to the prescribed temperature, at which a part of ice fixing the form of the frozen organism specimen 12 is melted to allow the tissue section 16 to adhesively abut on the tape 32, e.g., 0-40° C. (preferably 10-30° C.), so that the tip part of the tissue section 16, which has contacted the tape 32, is adhered onto the tape 32.

The tissue section 16, whose tip part has been adhered on the tape 32, is moved in the direction of the arrow with the tape 32 and cut off from the frozen organism specimen 12 with the movement of the jig 25 in the direction of the arrow A.

At that time, the control section 21 synchronizes the servo motor (not shown) for driving the driving roller 44, which draws the tape 32, with the servo motor 33 for moving the jig 25 in the direction of the arrow A, so that the slicing speed of the tissue section 16 can synchronize with the running speed of the tape 32. With this synchronization, a part of the sliced tissue section 16 is moved together with the tape 32, so that other sliced parts of the tissue section 16 can be continuously adhered onto the tape 32 [FIG. 3D]. Therefore, the entire tissue section 16 can be adhered on the tape 32 without forming creases, etc.

Figure 3D:
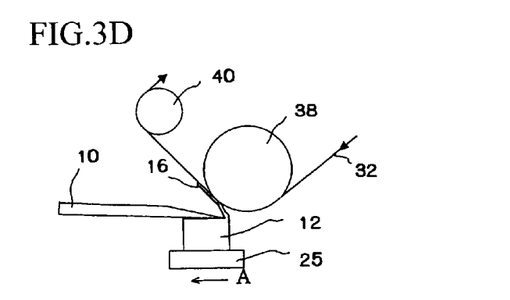
Figure 3E:
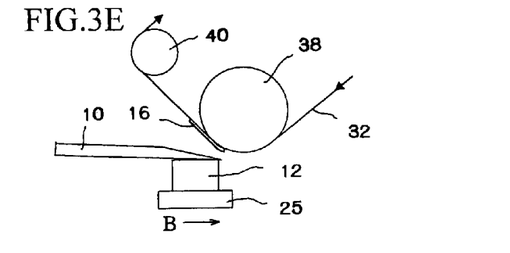

When the tissue section 16 is completely cut off from the frozen organism specimen 12, the tissue section 16, which is wholly adhered on the tape 32, can be manufactured, then the jig 25 is moved in the reverse direction of the arrow A until reaching the position shown in FIG. 3A [FIG. 3E]. During this action, a clearance is formed between the cutting surface of the knife 10 and the frozen organism specimen 12 so as to prevent an interference of the knife 10 and the frozen organism specimen 12.

When the device returns to the state shown in FIG. 3A and starts the next slice, the servo motor 24 is started so as to move the frozen organism specimen 12 the prescribed distance and define the thickness of the tissue 16 sliced off from the frozen organism specimen 12.

By repeating the steps shown in FIGS. 3A-3E, a plurality of the tissue sections 16 can be adhered on the tape 32 in slicing order.

The tape 32, on which the tissue sections 16 are adhered, is drawn by the driving roller 44 and wound on the collecting roller (not shown).

The tissue sections 16, which are adhered on the tape 32 wound on the collecting roller, are stained, for microscopic observation, in a state such that they are adhered on the long tape 32 or the tape 32 are cut to individually separate the tissue sections 16.

By using the device shown in FIG. 1, a plurality of the tissue sections 16, which are made by continuously slicing the frozen organism specimen 12, can be manufactured by an inexperienced worker, therefore microscopic samples and samples for optical analysis can be easily manufactured. Even in clinics employing no experienced workers capable of slicing organism specimens without forming creases, rapid pathological examinations of the frozen organism specimens 12 can be performed.

Further, the tissue sections 16 are automatically sliced off from the frozen organism specimen 12 in the insulating box 62, in which temperature is maintained and air is circulated, so that there is no risk of infection from the frozen organism specimen 12.

The tissue section 16 can be adhered onto the tape 32 without pressing the tape 32 onto the frozen organism specimen 12. The disadvantages of the conventional methods disclosed in the patent gazettes, such as breaking tissue cells of the tissue section 16, which is caused by pressing the tape 32 thereonto, and uneven thickness of the tissue section 16, can be prevented, further the rate-controlling stage of manufacturing a microscopic sample can be prevented when the tissue section 16 is adhered onto the tape 32.

In the actions shown in FIGS. 3A-3E of the device shown in FIG. 1, preferably the servo motor 22 is controlled to make the speed of slicing the tissue section 16 during the steps shown in FIGS. 3A-3C slower than the speed of slicing the tissue section 16 in the step shown in FIG. 3D. By controlling the servo motor 22, degree of curling the tissue section 16 toward outside of the slicing surface of the frozen organism specimen 12 can be controlled. In this case too, preferably the servo motor for driving the driving roller 44 is controlled to synchronize the running speed of the tape 32 with the speed of slicing the tissue section 16.

In the device shown in FIG. 1, the tape 32, on which the tissue sections 16 are adhered, is once wound on the collecting roller, but the tissue sections 16, which have been continuously adhered on the tape 32, may be stained without winding thereon.

The tissue sections 16, which are adhered on the tape 32 and stained, may be adhered on substrates, e.g., slide glass, so as to protect them or use them as microscopic samples.

Further, in the device shown in FIG. 1, the knife 10 and the frozen organism specimen 12 may be separately cooled so as to maintain temperature of the knife 10 and the frozen organism specimen 12 between $-1°$ C.$-−40°$ C. In this case, cooling pipes, to which refrigerants are supplied, or Peltier elements may be individually provided to the cylinder 11, to which the knife 10 is attached, and the jig 25, to which the frozen organism specimen 25 is fixed. If the knife 10 and the frozen organism specimen 12 can be separately cooled to the prescribed temperature from the atmosphere in which they are provided, controlling temperature of the insulating box 62, which is performed by the heat exchanging tubes 65 and 66 and the temperature control unit 64, is not required.

The device shown in FIG. 1 manufactures the tissue sections 16 from the frozen organism specimen 12, but the device is capable of manufacturing the tissue sections 16 by slicing an organism specimen 12, whose form is fixed by using an embedding agent, e.g., paraffin, whose melting point is higher than room temperature.

If the device shown in FIG. 1 manufactures the tissue sections 16 by slicing the organism specimen 12, whose form is fixed by using an embedding agent, e.g., paraffin, whose melting point is higher than room temperature, the atmosphere for slicing the organism specimen 12 need not be cooled. Therefore, the temperature control unit 64 for cooling air in the insulating box 62 is turned off, and supplying the refrigerants to the heat exchanging tubes 65 and 66 are stopped while manufacturing the tissue sections 16 by slicing the embedded organism specimen 12.

In the device, the heater 60, which is provided in the insulating box 62, is used as the temperature adjusting means, which adjusts the temperature difference between the tape 32 and the organism specimen 12, so as to adhere the tip part of the tissue section 16 onto the tape 32.

When the embedded organism specimen 12 passes the close roller 38, the heater 60 melts a part of the embedding agent, which fixes the form of the organism specimen 12, so as to allow the tissue section 16 to adhesively abut on the tape 32; for example, the embedding agent is paraffin whose melting point is 60° C., the tape 32 is heated to 65-70° C.

Note that, since the heater 60 is provided in the insulating box 62, if inner temperature of the insulating box 62 rises higher than prescribed temperature, the inner temperature of the insulating box 62 may be maintained 10-25° C. by the temperature control unit 64.

Figure 4:
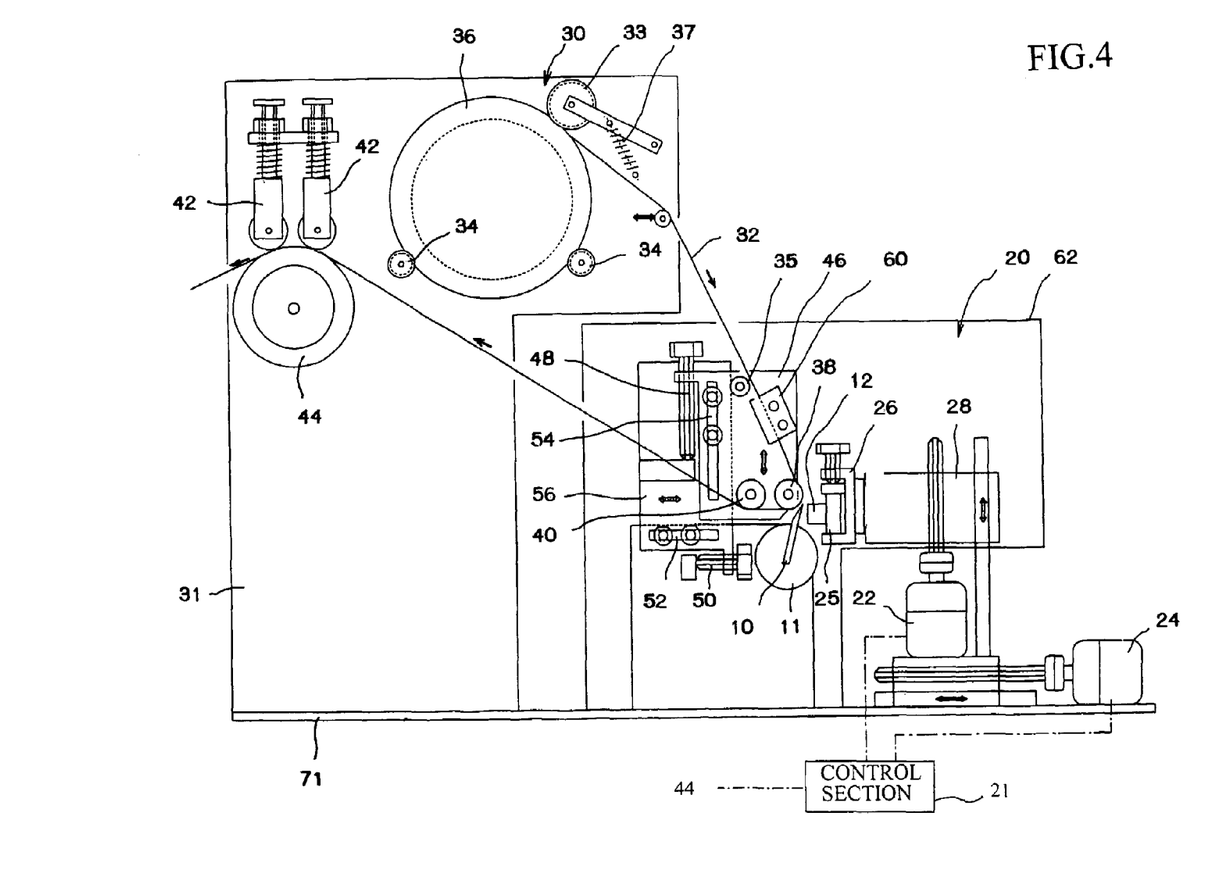
FIG. 4 is a schematic view of a tissue section manufacturing device of another embodiment.

Another tissue section manufacturing device, which is capable of manufacturing the tissue section 16 by slicing the organism specimen 12, which is embedded by an embedding agent whose melting point is higher than room temperature, e.g., paraffin, is shown in FIG. 4.

In the device shown in FIG. 4, the temperature control unit 64 and the heat exchanging tubes 65 and 66, which are used in the device shown in FIG. 1 so as to circulate air in the insulating box 62 and maintain temperature therein, are omitted.

Thus, the heater 60 is used, as the means for adjusting the temperature difference between the tape 32 and the organism specimen 12, so as to adhere the tip part of the tissue section 16 onto the tape 32.

When the embedded organism specimen 12 passes the close roller 38, the heater 60 melts a part of the embedding agent, which fixes the form of the organism specimen 12, so as to allow the tissue section 16 to adhesively abut on the tape 32; for example, the embedding agent is paraffin whose melting point is 60° C., the tape 32 is heated to 65-70° C.

Since the heater is provided in the insulating box 62, if inner temperature of the insulating box 62 rises higher than prescribed temperature, the inner temperature of the insulating box 62 may be maintained at prescribed temperature by means for ventilating air in the insulating box 62 or detaching the insulating box 62.

Note that, in FIG. 4, the structural elements shown in FIG. 1 are assigned the same symbols of FIG. 1, and detail explanation is omitted.

In the above embodiments shown in FIGS. 1-4, the tape 32 is a transparent tape so as to use the tape 32 as a cover glass; if the tape 32 is not used as the cover glass, for example, the tissue section 16 adhered on the tape 32 is transferred onto a slide glass, the tape may be made of an opaque film.

In the device shown in FIG. 1, the tape 32 is heated by the heater 60 provided in the insulating box 62; if outer temperature of the insulating box 62 is high and the temperature of the tape 32, which passes the close roller 38, can be maintained the prescribed temperature at which the tissue section 16 is adhered onto the tape 32, the step of heating the tape 32 by the heater 60 can be omitted.

Further, if the tape 32 is continuously run between the step shown in FIG. 3E and the step shown in FIG. 3A, the tape 32 is wastefully consumed, so the servo motor for driving the driving roller 44 may be stopped between the step shown in FIG. 3E and the step shown in FIG. 3A so as to stop the wasteful consumption of the tape 32.

Note that, the organism specimens, which are treated in the devices shown in FIGS. 1 and 4, may be not only specimens cut off from animals' bodies, which are used in a field of medical science, but also specimens cut off from plants, which are used in a field of agriculture science.

Experiments

The present invention will be explained in detail with reference to results of experiments.

Experiment 1

In the device shown in FIG. 1, the tissue sections 16 were made by slicing the frozen organism specimen 12, which was cut off from a pig lung, liver or muscle.

The tape 32 used in the device shown in FIG. 1 was the transparent film tape 32, which was made of cellulose acetate and whose width was 24 mm; the organism specimen 12 was made by the steps of: cutting a piece off from a pig lung, liver or muscle; embedding the cut piece in carboxymethylcellulose as an ice crystal-inhibitor, and freezing the embedded piece.

The frozen organism specimen 12 was fixed to the jig 25, on which carboxymethylcellulose was applied, then the jig 25, to which the frozen organism specimen 12 had been fixed, was fixed to the clamper 26 of the holding section 28. The cylinder 11, to which the knife 10 was attached, was turned until the angle θ (see FIG. 2) between the slicing surface of the frozen organism specimen 12 fixed to the holding section 28 and the cutting surface of the knife 10 became 22.5 degree.

To cool the frozen organism specimen 12 and the part to which the knife 10 was fixed or attached, the refrigerant was applied to the heat exchanging tubes 65 and 66 so as to maintain temperature of the knife 10 between −16--20° C. and temperature of the holding section 28 between −21--25° C. Further, the temperature control unit 64 circulated air in the insulating box 62 so as to maintain inner temperature of the insulating box 62 between −15--25° C.

The position of the close roller shown in FIG. 1, whose diameter was 10 mm, was moved by the screws 48 and 50, which are provided to the plates 46 and 56, so as to adjust the distance C shown in FIG. 2 between the close roller 38 and the frozen organism specimen 12 (see FIG. 2) to 0.4 mm.

The tape 32 drawn from the tape cylinder 36 was engaged with the guide roller 35, the heater 60, the close roller 38, the guide roller 40, the driving roller 44 and the collecting roller (not shown) so as to wind the tape, then the servo motor 24 was driven so as to move the holding section 28, which had the clamper 26 for holding the jig 25 to which the frozen organism specimen 12 was fixed, the prescribed distance rightward and leftward and defined the thickness of the tissue sections 16, which were sliced off from the frozen organism specimen 12, 5 μm, further the driving roller 44 is rotated to start running the tape 32. The tape 32 was heated by the heater 60 provided in the insulating box 62 so as to maintain the temperature of the running tape 32, which was guided by the close roller 38, between 0-20° C.

Then, the servo motor 22 was driven so as to move the holding section 28 upward and downward, so that the tissue sections having the thickness of 5 μm were sliced off from the frozen organism specimen 12 by the knife 10. The servo motor 22 was synchronized with the servo motor driving the driving roller 44 so as to synchronize the running speed of the tape 32 with the slicing speed of the tissue sections 16, so that no creases were formed in the tissue section 16 adhered on the tape 32.

In this experiment, the speed of slicing the tissue sections 16, whose thickness was 5 μm, was 15 times/minute. During the slice, ratio (Vt/Vs) of the running speed (Vt) of the tape 32 to the moving speed (Vs) of the holding section 28 was adjusted to 0.9. As a result, a plurality of good tissue sections 16, which had no creases, were serially adhered on the tape 32 and arranged in the longitudinal direction thereof with separations.

Experiment 2

In this experiment, the speed of slicing the tissue sections 16, whose thickness was 5 μm, was 60 times/minute, but other conditions were the same as those of the experiment 1; the ratio (Vt/Vs) of the running speed (Vt) of the tape 32 to the moving speed (Vs) of the holding section 28 was 0.9 as well as the experiment 1. Front ends of some tissue sections 16 were broken, but they were usable as microscopic samples.

Experiment 3

In this experiment, the distance C shown in FIG. 2 between the close roller 38 and the frozen organism specimen 12 (see FIG. 2) to 2 mm, but other conditions were the same as those of the experiment 1. Marks existed in some tissue sections 16, but they were accepted.

Experiment 4

The tissue sections 16 were made in the device shown in FIG. 4 by the steps of: cutting a piece off from the organism specimen 12, e.g., pig lung, liver, muscle; fixing the piece by formalin; dehydrating the fixed piece by ethanol; penetrating the piece by xylene; and embedding the piece by paraffin, whose melting point was 60° C.

The tape 32 used in the device shown in FIG. 4 was the transparent film tape 32, which was made of cellulose acetate and whose width was 24 mm, the organism specimen 12, which was embedded by paraffin whose melting point was 60° C., was fixed to the jig 25, and the jig 25 was fixed to the clamper 26 of the holding section 28. The cylinder 11, to which the knife 10 was attached, was turned until the angle θ (see FIG. 2) between the slicing surface of the frozen organism specimen 12 fixed to the holding section 28 and the cutting surface of the knife 10 became 22.5 degree.

The position of the close roller shown in FIG. 4, whose diameter was 10 mm, was moved by the screws 48 and 50, which are provided to the plates 46 and 56, so as to adjust the distance C shown in FIG. 2 between the close roller 38 and the frozen organism specimen 12 (see FIG. 2) to 0.4 mm.

The tape 32 drawn from the tape cylinder 36 was engaged with the guide roller 35, the heater 60, the close roller 38, the guide roller 40, the driving roller 44 and the collecting roller (not shown) so as to wind the tape, then the servo motor 24 was driven so as to move the holding section 28, which had the clamper 26 for holding the jig 25 to which the organism specimen 12 was fixed, the prescribed distance rightward and leftward and defined the thickness of the tissue sections 16, which were sliced off from the organism specimen 12, 5 μm, further the driving roller 44 is rotated to start running the tape 32. The tape 32 was heated by the heater 60 provided in the insulating box 62 so as to maintain the temperature of the running tape 32, which was guided by the close roller 38, between 65-70° C.

Then, the servo motor 22 was driven so as to move the holding section 28 upward and downward, so that the tissue sections 16 having the thickness of 5 μm were sliced off from the organism specimen 12 by the knife 10. The servo motor 22 was synchronized with the servo motor driving the driving roller 44 so as to synchronize the running speed of the tape 32 with the slicing speed of the tissue sections 16, so that no creases were formed in the tissue section 16 adhered on the tape 32.

In this experiment, the speed of slicing the tissue sections 16, whose thickness was 5 μm, was 15 times/minute. During the slice, ratio (Vt/Vs) of the running speed (Vt) of the tape 32 to the moving speed (Vs) of the holding section 28 was adjusted to 0.9. As a result, a plurality of good tissue sections 16, which had no creases, were serially adhered on the tape 32 and arranged in the longitudinal direction thereof with separations.

Note that, the insulating box 62 was ventilated to maintain inner temperature of the insulating box 62 between 15-25° C.

EFFECTS OF THE INVENTION

By the present invention, good tissue sections can be easily and safely made from an organism specimen by an inexperienced worker. Since microscopic samples can be easily manufactured, pathological examinations can be performed in clinics employing no experienced workers so that patients can be properly cured.

Even in clinics in rural and remote areas, e.g., island, in which no pathologic doctors are hired, microscopic images of manufactured samples can be sent to pathologic doctors via a communication network, e.g., internet, so that patients can be properly cured.

Further, even inexperienced researchers in other fields, e.g., life science, who are not familiar with manufacturing morphologic samples, can easily manufacture observation samples.

The invention claimed is:

1. A method for manufacturing a tissue section, which is used for a sample for observation by a microscope, comprises the steps of:
    slicing an organism specimen along a slicing surface to form the tissue section in an atmosphere of air, a form of the organism specimen having been fixed by freezing or by using an embedding agent;
    adjusting a distance between the slicing surface of the organism specimen and one side of a film and a temperature difference between the organism specimen and the film when the slicing of the organism specimen is started, thereby a tip part of the tissue section curling to the outside of the slicing surface of the organism specimen is allowed to adhesively abut on one side of the film running apart from the slicing surface of the organism specimen; and
    running the film at a speed in synchronism with a slicing speed of the tissue section after the tip part of the tissue section is allowed to adhesively abut on the one side of the film, thereby the entire tissue section cut off from the organism specimen can be adhered onto the one side of the film,
    wherein a plurality of rollers including a close roller, which is provided nearest to the slicing surface of the organism specimen, is provided in a film running path, and the distance between the slicing surface of the organism specimen and the one side of the film is adjusted by moving the close roller to and away from the slicing surface of the organism specimen; said slicing step occurring while said close roller is held in a fixed position.

2. The method according to claim 1, wherein the temperature difference between the organism specimen and the film is adjusted by adjusting temperature of the film and/or temperature of an atmosphere, in which the organism specimen is sliced.

3. The method according to claim 1, wherein temperature of the film is adjusted to temperature, at which a part of an ice or the embedding agent for fixing the form of the organism specimen melts and the tissue section is adhered onto the film.

4. The method according to claim 1, wherein temperature of an atmosphere, in which the organism specimen is sliced, is adjusted so as to hold the fixed form of the organism specimen.

5. The method according to claim 1, wherein a center of the close roller is moved on a bisector line of an intersection angle between a line extended from a cutting surface of a cutting tool, which intersects a line extended from the slicing surface of the organism specimen, and the line extended from the slicing surface of the organism specimen.

6. The method according to claim 1, wherein the film running speed with respect to the slicing speed of the tissue section is adjusted so as not to form creases in the tissue section and break the tissue section.

7. The method according to claim 1, wherein ratio (Vt/Vs) of the film running speed (Vt) to the slicing speed (Vs) of the tissue section is 1.2-0.8.

8. The method according to claim 1, wherein the film is a transparent film.

9. A method for manufacturing a tissue section, which is used for a sample for observation by a microscope, comprising the stops of:

slicing an organism specimen along a slicing surface to form the tissue section, with a knife having a front end part whose one side face is formed into an angled surface, in an atmosphere of air, a form of the organism specimen having been fixed by freezing or by using an embedding agent;

adjusting a shortest distance between a close roller, which can be moved toward the slicing surface of the organism specimen and which guides a film running apart from the slicing surface, and a slice starting point, at which a front end of the angled surface of the knife contacts the slicing surface of the organism specimen at a prescribed angle and starts the slicing, by moving a center of the close roller to and away from the slice starting point, thereby a tip part of the tissue section curling to an outside of the slicing surface of the organism specimen is allowed to contact one side of the film when the slicing of the organism specimen is started;

adjusting temperature between the organism specimen and the film so as to make the tip part of the tissue section, which has been contracted the outside of the film, adhesively abut on the film; and running the film at a speed in synchronism with a slicing speed of the tissue section so as to adhere the entire tissue section cut off from the organism specimen onto the one side of the film with slicing the tissue section, whose tip part has been adhered on the one side of the film, by moving the organic specimen, in a prescribed direction, in a state of holding the close roller and the knife at prescribed positions.

10. A device for manufacturing a tissue section, which is used for a sample for observation by a microscope, comprising:

means for slicing an organism specimen along a slicing surface to form the tissue section in an atmosphere of air, a form of the organism specimen having been fixed by freezing or by using an embedding agent; and means for running a film apart from the slicing surface of the organism specimen;

means for adjusting a distance between the slicing surface of the organism specimen and one side of the film so as to make a tip part of the curling tissue section contact with the outside of the slicing surface of the organism specimen when the slicing of the organism specimen is started;

means for adjusting temperature between the organism specimen and the film so as to make the tip part of the tissue section, which has been contacted the outside of the film, adhesively abut on the film; and means for synchronizing a slicing speed of the tissue section, whose tip part has been adhered on the one side of the film, and a running speed of the film so as to adhere the entire tissue section cut off from the organism specimen onto the one side of the film, wherein said distance adjusting means has a plurality of rollers, provided in a film running path and which includes a close roller provided nearest to the slicing surface of the organism specimen, and the close roller is capable of moving to and away from the slicing surface of the organism specimen;

the device for manufacturing a tissue section further comprising means for fixing the close roller in position during slicing of the organism specimen.

11. The device according to claim 10, wherein said temperature adjusting means adjusts temperature of the film and/or temperature of an atmosphere, in which the organism specimen is sliced.

12. The device according to claim 10, further comprising means for adjusting temperature of the film to temperature, at which a part of an ice or the embedding agent for fixing the form of the organism specimen melts and the tissue section is adhered onto the film, said temperature adjusting means being provided in a film running path.

13. The device according to claim 10, further comprising means for adjusting temperature of an atmosphere, in which the organism specimen is sliced, so as to hold the fixed form of the organism specimen.

14. The device according to claim 10, wherein a center of the close roller is moved on a bisector line of an intersection angle between a line extended from a cutting surface of a cutting tool, which intersects a line extended from the slicing surface of the organism specimen, and the line extended from the slicing surface of the organism specimen.

15. The device according to claim 10, wherein said synchronizing means has a control section, which controls said running means and said slicing means to adjust the film running speed with respect to the slicing speed of the tissue section so as not to form creases in the tissue section and break the tissue section.

16. The device according to claim 15, wherein the control section controls said running means and said slicing means so as to make ratio (Vt/Vs) of the film running speed (Vt) to the slicing speed (Vs) of the tissue section 1.2-0.8.

17. The device according to claim 10, wherein the film is a transparent film.

18. A device for manufacturing a tissue section, which is used for a sample for observation by a microscope and which is formed by slicing an organism specimen, whose form has been fixed by freezing or by using an embedding agent, along a slicing surface to form the tissue section in an atmosphere of air, comprising:

a knife for slicing the organism specimen along the slicing surface, the knife having a front end part whose one side face is formed into an angled surface;

means for running a film, which is guided by a close roller capable of moving to and away from the slicing surface of the organism specimen, apart from the slicing surface of the organism specimen;

means for adjusting a shortest distance between the close roller, which can be moved toward the slicing surface of the organism specimen which guides a film running apart from the slicing surface, and a slice starting point, at which a front end of the angled surface of the knife contacts the slicing surface of the organism specimen at a prescribed angle and starts the slicing, by moving a center of the close roller to and away from the slice starting point so as to allow a tip part of the tissue section curling to an outside of the slicing surface of the organism specimen contact one side of the film;

means for adjusting temperature between the organism specimen and the film so as to make the tip part of the tissue section, which has been contacted the outside of the film, adhesively but on the film; and means for slicing the tissue section by moving the organic specimen, in a prescribed direction, in a state of holding the close roller and the knife at prescribed positions and for running the film at a speed in synchronism with a slicing speed of the tissue section so as to adhere the entire tissue section cut off from the organism specimen onto the one side of the film.

* * * * *